United States Patent [19]

Tsuji et al.

[11] Patent Number: 5,114,232

[45] Date of Patent: May 19, 1992

[54] MOVING MIRROR VELOCITY DETECTION IN AN INTERFERENCE SPECTROPHOTOMETER

[75] Inventors: Fumio Tsuji; Osamu Yoshikawa, both of Kyoto, Japan

[73] Assignee: Shimadzu Corporation, Kyoto, Japan

[21] Appl. No.: 635,023

[22] Filed: Dec. 28, 1990

[30] Foreign Application Priority Data

Dec. 29, 1989 [JP] Japan .................................. 1-342371

[51] Int. Cl.$^5$ ................................................. G01B 9/02
[52] U.S. Cl. ..................................... 356/346; 356/319
[58] Field of Search ................. 356/346, 319; 250/339

[56] References Cited

U.S. PATENT DOCUMENTS

| | | | |
|---|---|---|---|
| 4,511,986 | 4/1985 | Bellar | 356/346 |
| 4,799,001 | 1/1989 | Burch | 356/346 |
| 4,847,878 | 7/1989 | Badeau | 356/346 |

Primary Examiner—Samuel A. Turner
Assistant Examiner—Richard E. Kurtz, II
Attorney, Agent, or Firm—Armstrong, Nikaido, Marmelstein, Kubovcik & Murray

[57] ABSTRACT

There is disclosed an interference spectrophotometer which collects data while monitoring the position of a movable mirror by providing quadrature control to accurately perform coherent addition of data. The spectrophotometer includes a main interferometer, a control interferometer, a sliding controller controlling movement of the movable mirror, an A/D converter converting analog data obtained by the main interferometer into digital form, a register for holding data obtained by one scan of the movable mirror, a memory for accumulating data obtained by numerous scans of the movable mirror, an up/down counter receiving the output signals from two detectors included in the control interferometer, and a decision part. When the counter's value varies, the counter causes the A/D converter to perform its A/D conversion. Then, the decision part checks the counter's value after the A/D conversion. If this value differs from the count value obtained prior to the A/D conversion, the data held in the register is discarded.

2 Claims, 9 Drawing Sheets

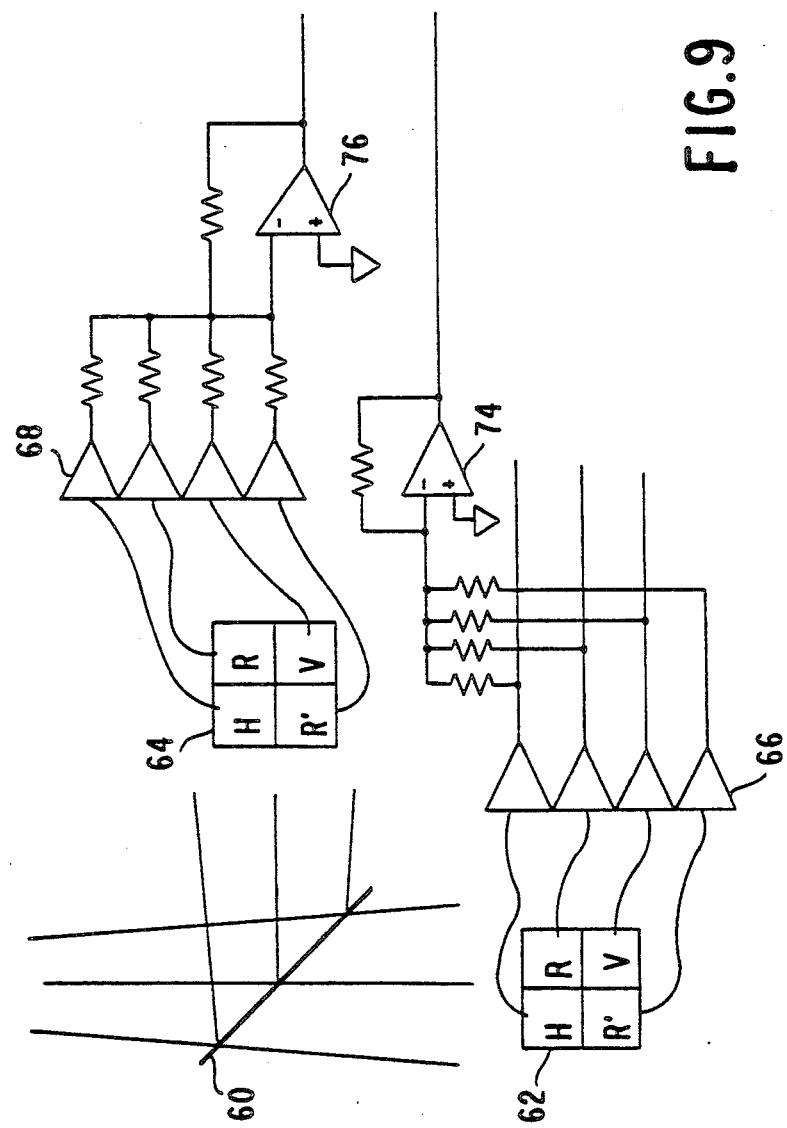

MOVING MIRROR VELOCITY DETECTION IN AN INTERFERENCE SPECTROPHOTOMETER

FIELD OF THE INVENTION

The present invention relates to an interference spectrophotometer such as a Fourier transform infrared spectrophotometer.

BACKGROUND OF THE INVENTION

Interference spectrophotometers such as Fourier transform infrared (FT IR) spectrophotometers are used to make qualitative and quantitative analyses of various substances including organic and inorganic substances as well as high-molecular materials and semiconductor materials.

An interference spectrophotometer has a main interferometer for investigating samples and a control interferometer for starting collection of data from the main interferometer and for stabilizing the speed at which the movable mirror is slid. The control interferometer provides quadrature control to detect the position of the movable mirror. For this purpose, a phase plate such as a $\lambda/8$ plate is installed between the beam splitter and the fixed mirror. Interference signals meeting at the beam splitter are separated into P waves and S waves by a polarizing beam splitter. The polarized components are detected by their respective detectors, and the position of the movable mirror is determined from the phase relation between the output signals from the detectors and from the wave number.

When measurements are made with an interference spectrophotometer, it is necessary to move the movable mirror at a constant speed in one direction. If external disturbance such as vibration is imparted to the instrument, the sliding movement of the movable mirror is disturbed. In an interference spectrophotometer, the movable mirror is reciprocated plural times to improve the signal-to-noise ratio of data obtained by measurements. Data obtained at the same position of the movable mirror is accumulated. This procedure is called coherent addition. If the sliding movement of the movable mirror is disturbed by external disturbance, then the coherent addition is destroyed in accumulating data. As a result, the accumulated data will be inaccurate. The technique for detecting the position of the movable mirror by providing quadrature control is essential for coherent addition.

SUMMARY OF THE INVENTION

It is an object of the invention to provide an interference spectrophotometer which collects data while monitoring the position of a movable mirror to accurately perform coherent addition.

During measurement, the novel instrument monitors the total count obtained by an up/down counter by providing quadrature control, whereby the disturbance of sliding movement of the movable mirror is detected with sensitivities of the order of the wavelength of the control interferometer.

Other objects and features of the invention will appear in the course of the description thereof which follows.

BRIEF DESCRIPTION OF THE DRAWINGS

FIG. 9 is a diagram of the polarizing beam splitter and the detectors included in the spectrophotometer shown in FIG. 2.

DETAILED DESCRIPTION OF THE INVENTION

Figure 1:
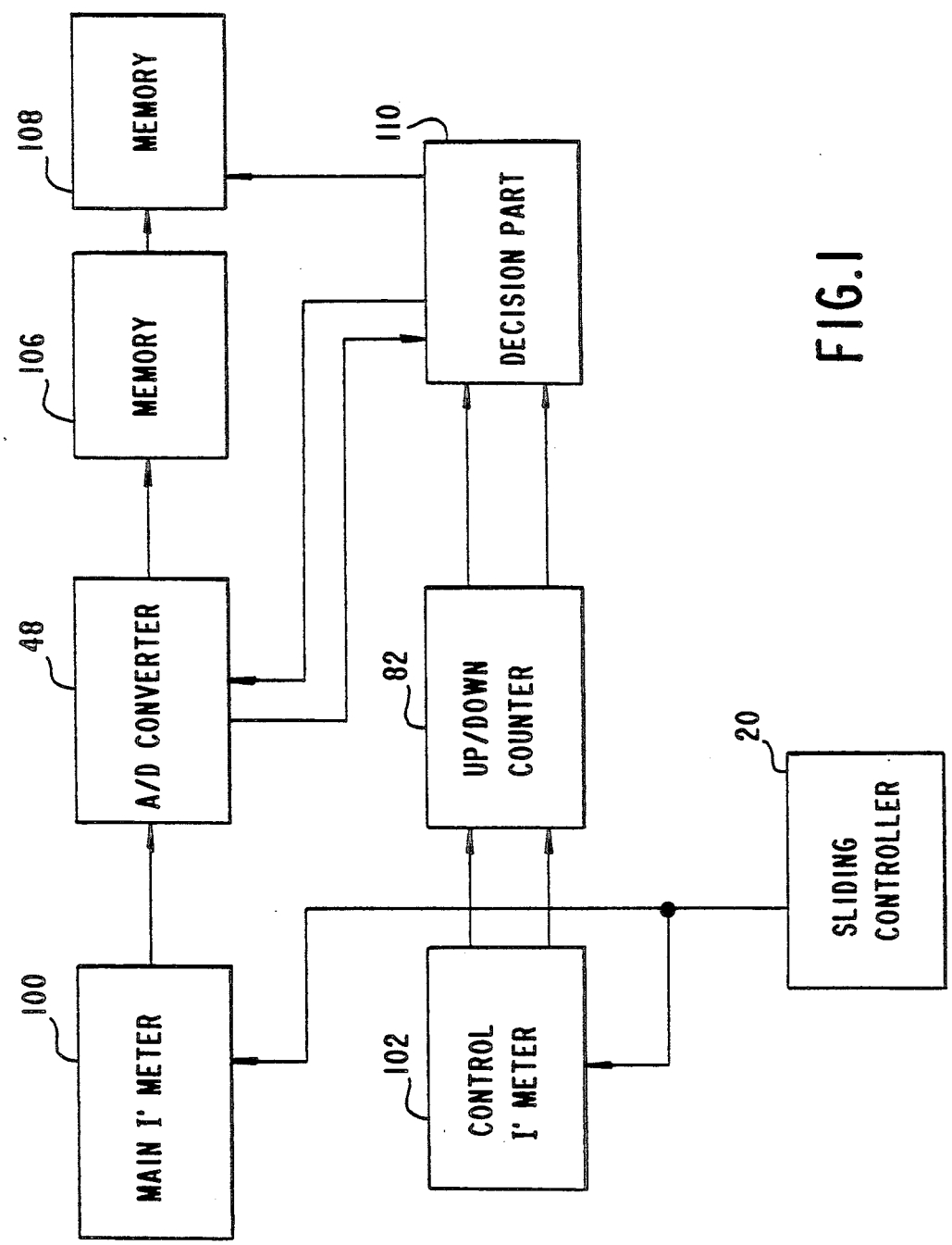
FIG. 1 is a schematic block diagram of an interference spectrophotometer according to the invention.

Referring to FIG. 1, there is shown an interference spectrophotometer according to the invention. This spectrophotometer comprises a main interferometer 100, a control interferometer 102, a sliding controller 20, an analog-to-digital converter 48, an up/down counter 82, a first memory 106 holding data, a second memory 108 storing accumulated data, and a decision part 110.

The main interferometer 100 shares a beam splitter, a fixed mirror, and a movable mirror with the control interferometer 102. Sliding movement of the movable mirror is controlled by the sliding controller 20. Data obtained by the main interferometer 100 is converted into digital form by the A/D converter 48. Data obtained by one scan of the movable mirror is held in the first memory 106. The up/down counter 82 receives the output signals from two detectors used for quadrature control, the detectors being included in the control interferometer 102. The decision part 110 causes the converter 48 to convert its input analog signal into digital form when the value of the up/down counter 82 varies. After the A/D conversion, the decision part 110 checks the counter's value. If this value differs from the count value obtained when the A/D conversion was started, then the decision part 110 determines that the sliding movement of the movable mirror was abnormal. If the sliding movement of the mirror is determined to be normal by the decision part 110, then it adds the data held in the memory 106 to the data stored in the memory 108. If the sliding movement of the mirror is regarded as abnormal, then the decision part does not accumulate the data but discards the data held in the memory 106.

The up/down counter 82 which receives quadrature control signals is incremented or decremented whenever the movable mirror moves a distance of $\lambda/2$, where $\lambda$ is wavelength of 632.8 nm for a He-Ne laser. It takes several microseconds to read the output signal from the A/D converter 48 and to execute the algorithm stored in the first memory 106. If the speed of the sliding mirror is appropriate, the analog signal applied to the converter 48 is converted into digital form when the value obtained by the counter 82 is varied, i.e., at a sampling point. After the A/D conversion, the counter's value should agree with the count value obtained prior to the A/D conversion. If they do not agree, it follows that the movable mirror did not move correctly. That is, the mirror moved in the correct direction but too fast, or it moved in the reverse direction. In either case, an error in the movement can be detected with sensitivities of the order of 1 $\mu$m by this method.

If the sliding movement of the mirror was adequate, data obtained by the present scan of the movable mirror is transferred from the first memory 106 to the second memory 108 to accumulate data. If the sliding movement of the mirror is determined to be abnormal, then data obtained by this measurement is discarded and no accumulation is performed. Thus, the integrity of coherent addition is maintained. If data is discarded continuously over plural scans, then the sliding movement is taken as incorrect movement. Then, this series of measurements can be stopped.

Figure 2:
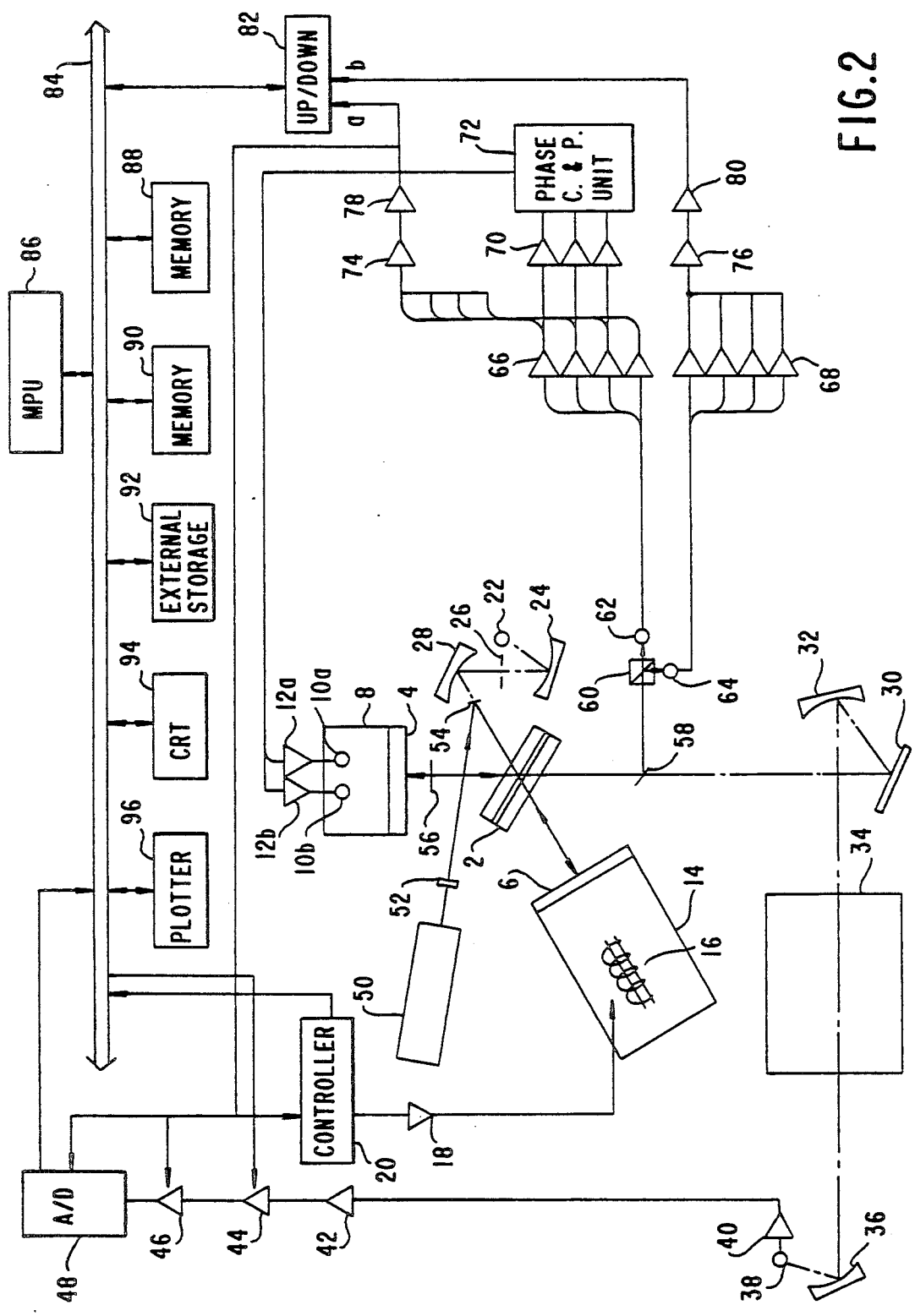
FIG. 2 is a diagram of one example of the spectrophotometer shown in FIG. 1.

Referring next to FIG. 2, there is shown a Fourier transform infrared spectrophotometer according to the invention. This instrument includes a beam splitter 2 acting also as a compensator, a fixed mirror 4, and a movable mirror 6. The splitter 2 is inclined at 45° to the normal to the fixed mirror 4 and also to the normal to the movable mirror 6.

The fixed mirror 4 is mounted on a block 8. Piezoelectric actuators 10a and 10b are also mounted on the block 8. The direction of the normal to the fixed mirror 4 can be changed by varying the voltages applied to the actuators 10a and 10b. Power amplifiers 12a and 12b apply the voltages to the actuators 10a and 10b, respectively.

The movable mirror 6 is carried on a sliding mechanism 14 having a linear motor 16 which moves the mirror 6 toward and away from the beam splitter 2. This motor 16 is supplied with electrical current from a power amplifier 18. A sliding controller 20 controls the linear motor 16 via the power amplifier 18.

An infrared radiation source 22 cooperates with the beam splitter 2, the fixed mirror 4, and the movable mirror 6 to constitute a main interferometer, thus forming an infrared spectrophotometric system. Infrared radiation emanating from the IR radiation source 22 passes to the beam splitter 2 via a converging mirror 24, an aperture 26, and a collimator mirror 28. Then, the radiation is modulated by this interferometer. The modulated radiation passes through a sample chamber 34 via a mirror 30 and a second converging mirror 32, is reflected off an ellipsoidal mirror 36, and falls on an infrared detector 38, where the radiation is converted into an electrical signal. The output signal from the detector 38 is amplified by a preamplifier 40. A filter 42, an automatic gain control amplifier 44, a sample-and-hold amplifier 46, and an analog-to-digital converter 48 are connected in series with the preamplifier 40. The A/D converter 48 acts to convert sampled signals into digital form.

A He-Ne laser 50 is installed to form a light source for a control interferometer. A concave or convex lens 52 increases the angle of divergence of the laser beam from the laser 50. The laser beam reflected off the lens 52 is caused to enter the beam splitter 2 by a half mirror 54. The beam is then reflected off the beam splitter 2 and off the fixed mirror 4, and returns to the splitter 2. A $\lambda/8$ plate 56 is located between the beam splitter 2 and the fixed mirror 4 to convert this returning beam from linearly polarized light into circularly polarized light. The $\lambda/8$ plate 56 is so placed that its axis of polarization is inclined at 45° to the plane of polarization of the incident laser beam. A polarizing beam splitter 60 is mounted to divide the interference light into two polarized components, or P waves S waves, after the interference light is modulated by this interferometer and reflected off the half mirror 58.

A quarter photodiode 62 that is a detector receives the polarized component passed through the polarizing beam splitter 60. Another quarter photodiode 64 receives the other polarized component reflected off the splitter 60 and detects the polarized component. As shown in FIG. 9, each of the photodiodes 62 and 64 is split into four light-receiving elements R, R', H, and V. Each photodiode is formed on a single semiconductor chip to prevent offset voltages or bias voltages from being developed between its light-receiving elements. The light-receiving elements of the photodiode 62 are connected with their respective preamplifiers 66. Similarly, the light-receiving elements of the photodiode 64 are connected with their respective preamplifiers 68.

The light-receiving element R of the four elements of either the photodiode 62 or 64 is used as a reference element. To make a dynamic alignment, the output signal from the reference element R, the output signal from the element H laterally adjacent to the element R, and the output signal from the element V vertically adjacent to the element R are applied to a phase comparison and processing unit 72 via their respective preamplifiers 66 and via their respective waveform shapers 70. The waveform shapers 70 change input signals into pulse trains. The output signal from the phase comparison and processing unit 72 is sent to the power amplifiers 12a and 12b.

To provide quadrature control, the output signals from the four light-receiving elements of the photodiode 62 are applied to a current-summing amplifier 74 via their respective preamplifiers 66. Likewise, the output signals from the four light-receiving elements of the photodiode 64 are supplied to another current-summing amplifier 76 via their respective preamplifiers 68. Waveform shapers 78 and 80 which change input signals into pulse trains are connected with the summing amplifiers 74 and 76, respectively. An up/down counter 82 receives the output pulses from the waveform shapers 78 and 80. The up/down counter 82 determines whether it is incremented or decremented, depending on the relationship between the phase of the two input signals. The counter 82 counts the number of input pulses and sends it along a CPU bus line 84. The output signal from the waveform shaper 78 is also sent to the sliding controller 20, to the sample-and-hold amplifier 46, and to the A/D converter 48.

An MPU 86, a memory 88 storing programs, a memory 90 storing data, an external storage 92, a CRT 94, a plotter 96, the automatic gain control amplifier 44, the A/D converter 48, and the up/down counter 82 are connected with the CPU bus line 84.

The memories 106, 108, and the decision part 110 shown in FIG. 1 are realized by the memory 90 storing data, the memory 88 storing programs, and the MPU 86. The operation of this instrument is next described.

(A) Operation of the Control Interferometer

Figure 8:
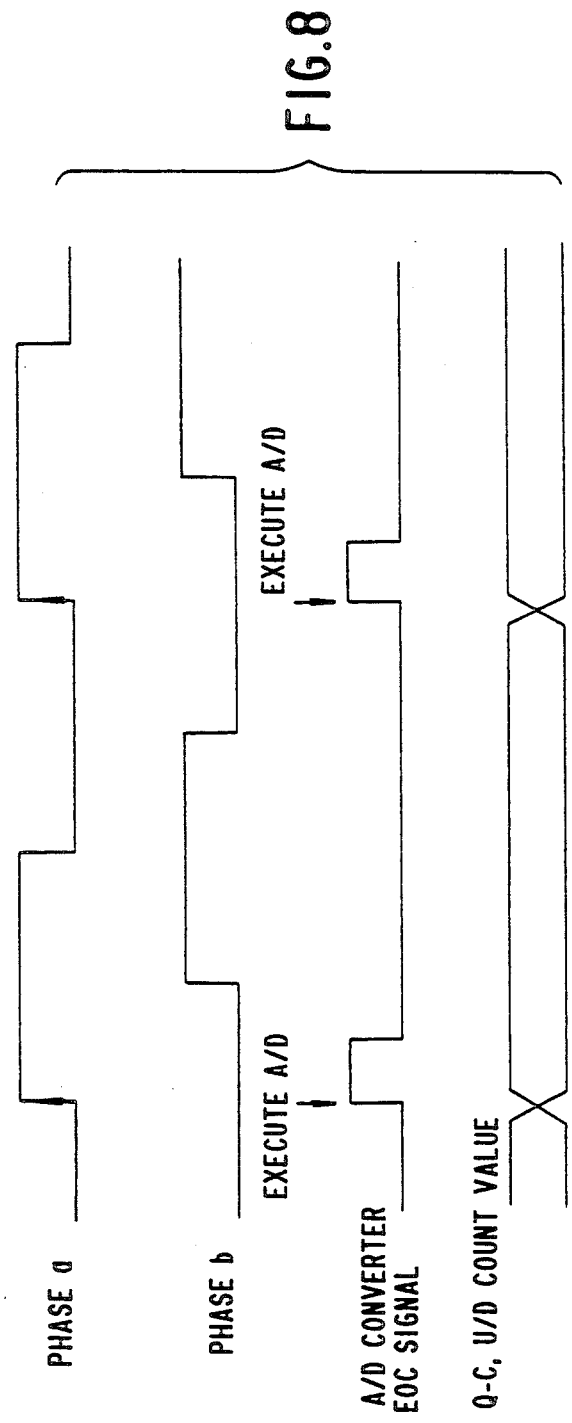
FIG. 8 is a timing diagram showing signals obtained by quadrature control, the output signal from an A/D converter, and the timing at which an up/down counter is operated.

The interference laser beams which are divided by the polarizing beam splitter 60 and out of phase with each other are received by the photodiodes 62 and 64, respectively. The waveforms of the output signals from the photodiodes 62 and 64 are modified to produce pulse signals. These pulse signals are accepted as two inputs a and b to the up/down counter 82. This counter 82 determines whether it is incremented or decremented, depending on the relation of the phases of the input signals. In particular, when the movable mirror 6 is moving toward the beam splitter 2, one signal a leads the other signal b by phase of 90°, as shown in FIG. 8. Conversely, when the mirror 6 is moving away from the beam splitter 2, the signal a lags the signal b by a phase of 90°. The number of input pulses counted by the up/down counter 82 depends on the position of the movable mirror 6. The output signal from the counter 82 is fed via the bus line 84 to the MPU 86, which detects abnormal vibration of the movable mirror if it occurs. Also, the output signal from the counter 82 is used when an interferogram is integrated in infrared spectroscopy.

The sliding controller 20 controls the voltage applied to the linear motor 16 via the power amplifier 18 in such a way that the frequency of the output signal from the photodiode 62 is kept constant. The signal a from the waveform shaper 78 is also employed by the sample-and-hold amplifier 46 as a sampling signal. In addition, the signal a is used as a start signal for causing the A/D converter 48 to start its analog-to-digital conversion.

When the interference conditions of the interferometer are good, the output signal γ from the reference light-receiving element R of the four-split photodiode 62 and the output signal h from other light-receiving element H or the output signal υ from the element V are in phase. When the interference conditions are inferior, they are out of phase. To make a dynamic alignment, the output signals from the three elements R, H, V of the four-split photodiode 62 are amplified, modified in waveform, and applied to the phase comparison and processing unit 72. This processing unit 72 produces a voltage indicating a vertical or horizontal shift. This voltage from the unit 72 controls the voltages applied to the piezoelectric actuators 10a and 10b via the power amplifiers 12a and 12b, respectively. In this way, the conditions of the interferometer is stabilized in such a manner that the output signals from plural light-receiving elements of the four-split photodiode 62 are put in phase.

(B) Operation for Collection of Infrared Data

The radiation which is emitted from the IR radiation source 22, modulated by the interferometer, and passed through the sample chamber 34 impinges on the IR detector 38, where the radiation is converted into an electrical signal. This signal is supplied to the preamplifier 40, the filter 42, and the automatic gain control amplifier 44 in this order. The output signal from the amplifier 44 is sampled by the sample-and-hold amplifier 46 and converted into digital form by the A/D converter 48. The output signal from the A/D converter 48 is sent along the bus line 84.

As the movable mirror 6 is moved, an interferogram is created. The A/D converter 48 is started to convert its input analog signal into digital form in response to the signal a which is an interference signal produced from the control interferometer. The present position of the movable mirror 6 is detected on a real-time basis by quadrature control. This signal indicating the present position is produced by the up/down counter 82 and constantly monitored by the MPU 86 to know the starting point and the end point of collection of data from the interferogram. Data is collected in two opposite directions of the movable mirror 6.

Figure 3:
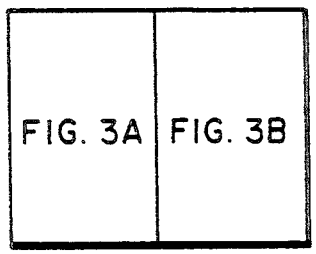
FIGS. 3, 3a, 3b, 4, 5, 6 are flowcharts illustrating the operation of the spectrophotometer shown in FIG. 2.
Figure 3A:
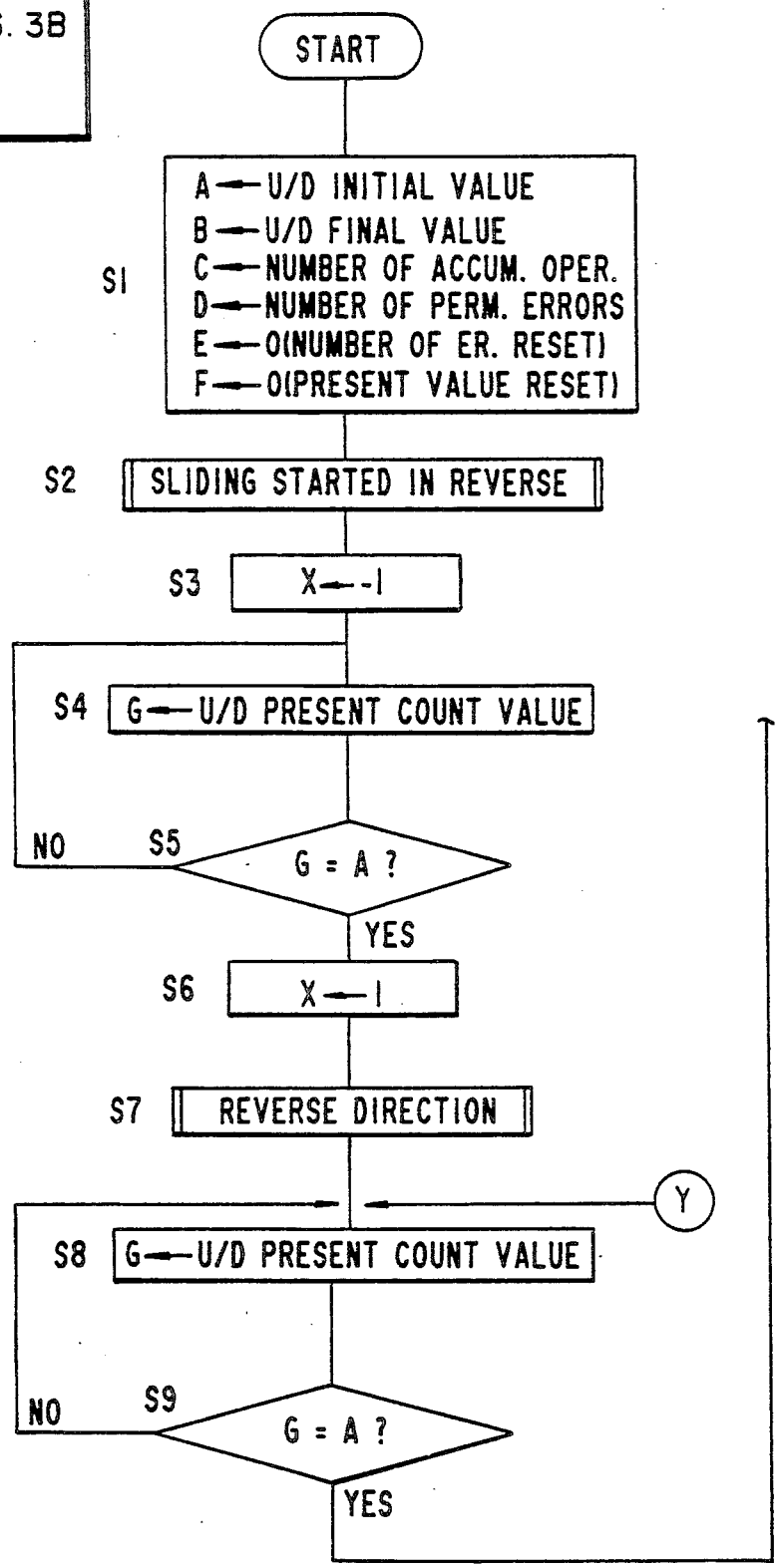
Figure 3B:
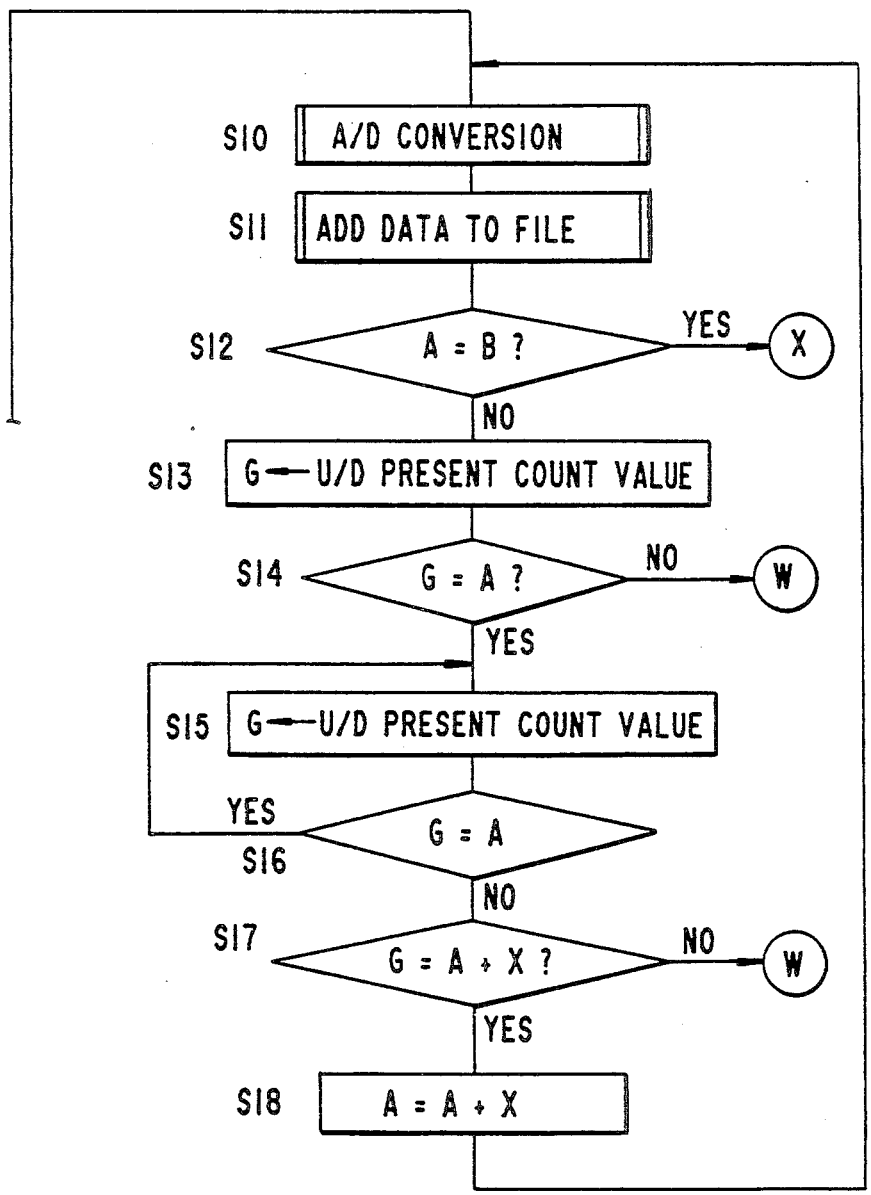
Figure 4:
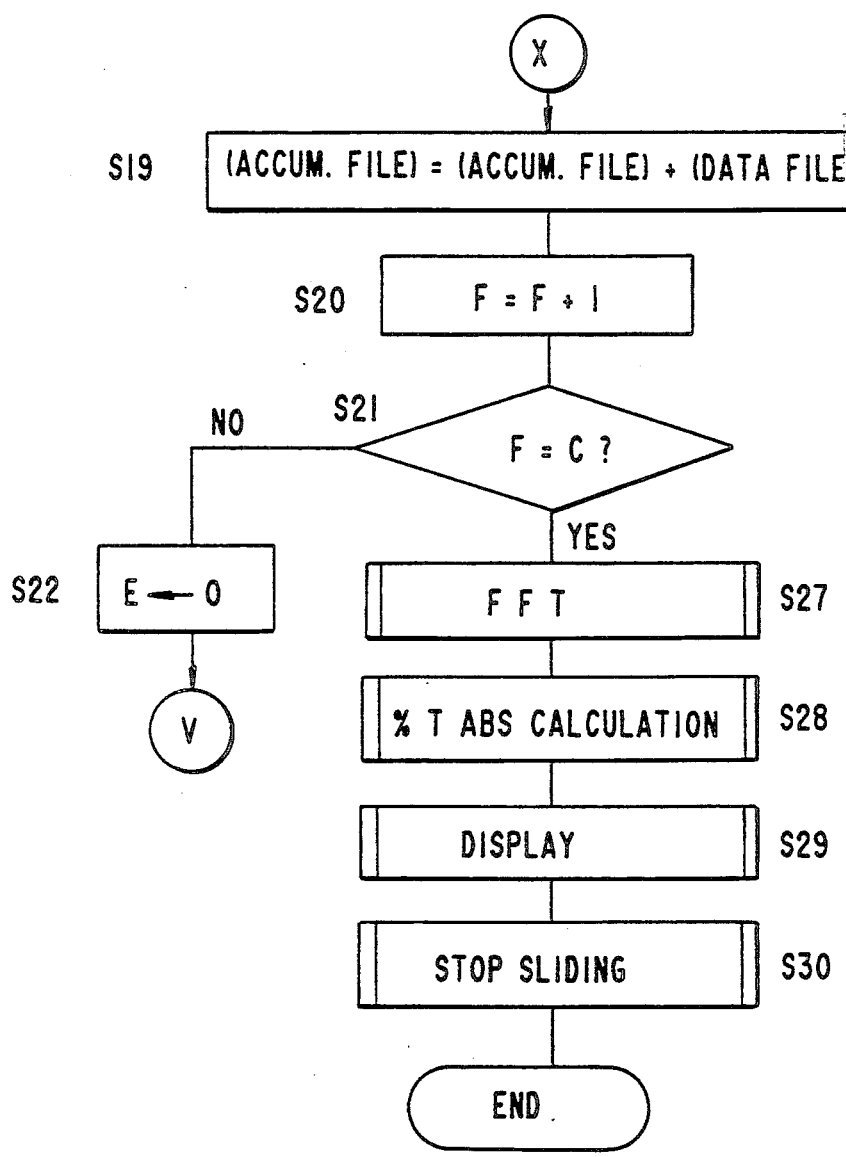
Figure 5:
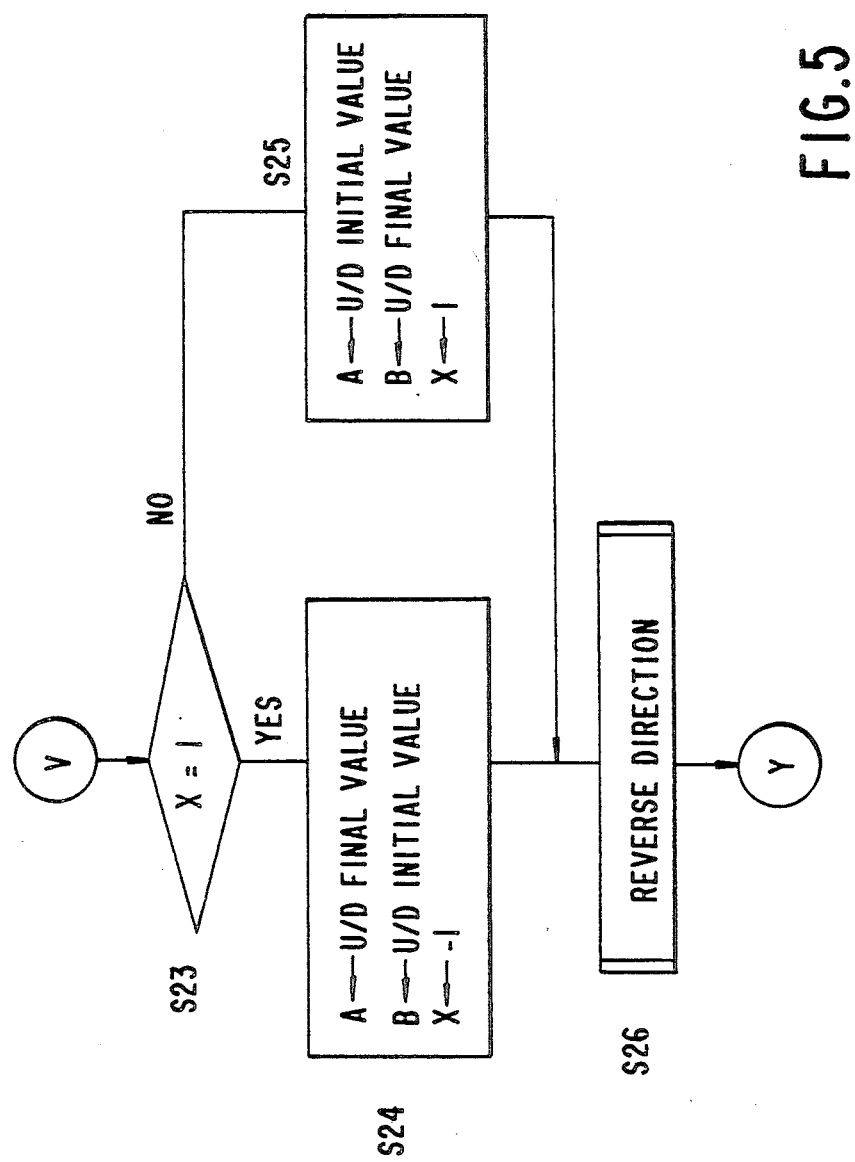
Figure 6:
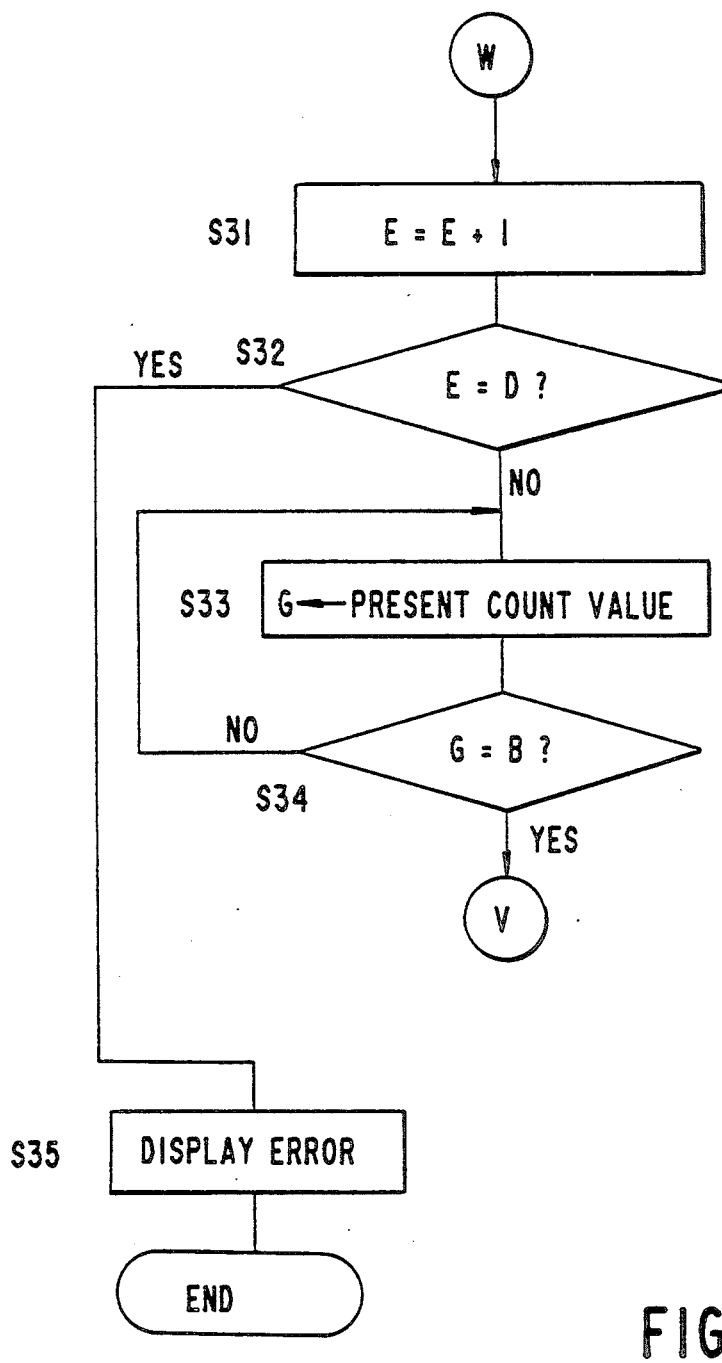
Figure 7:
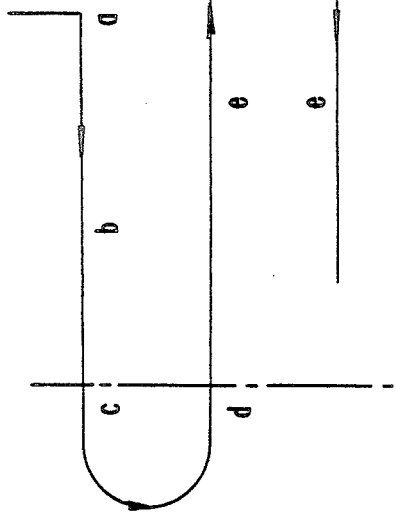
FIG. 7 is a diagram illustrating movement of the movable mirror used in the spectrophotometer shown in FIG. 2.

The manner in which infrared spectroscopy is effected is next described by referring to FIGS. 3-8. Referring to FIG. 3, the initial value A of up/down count, the final value B of the up/down count, the number of accumulative operations C, and the permissible number of errors D are set. The number of errors E and the present value of accumulation F are set to 0 (step 1). The up/down counter is reset at the position of center of burst. The initial value and the final value of the up/down count are determined by wave number division. Examples of them are shown in the table below. The user can select wave number division as a parameter.

| wave number division | 16/cm | 8/cm | 4/cm | 2/cm | 1/cm | 0.5/cm |
| --- | --- | --- | --- | --- | --- | --- |
| start value of U/D | −1024 | −2048 | −4096 | −8192 | −16384 | −32768 |
| final value of U/D | 1023 | 2047 | 4095 | 8091 | 16383 | 32767 |

The number of permissible errors indicates how many times data obtained by one series of samplings can be discarded. This number is preferably set to 2 or 3.

The MPU 86 specifies the direction of sliding movement of the movable mirror through the sliding controller 20, and the mirror is started to be slided at a constant speed (step 2). When the mirror is moved in a reverse direction, the up/down counter is decremented. When the mirror is moved in a forward direction, the counter is incremented. Then, a direction parameter X is set to −1 when the mirror is moved in the reverse direction and to +1 when the mirror is moved in the forward direction (step 3). The MPU 86 constantly monitors the value of the up/down counter 82 and waits until the present value G of the counter reaches the initial value A of up/down count (steps 4 and 5). The direction of sliding movement of the movable mirror is reversed (step 6 and 7). The MPU waits unit the mirror arrives at the starting position for measurement (steps 8 and 9). The movable mirror is moved from point a to point d in FIG. 7.

When the present value of the up/down counter reaches the initial value of up/down count, analog-to-digital conversion is carried out (step 10). The obtained data is added to the file of data about the interferogram (step 11). As shown in FIG. 8, analog-to-digital conversion is effected on leading edges of the signal a which is derived by shaping the waveform of the output signal from the detector 62. The up/down counter 82 is incremented or decremented also on the leading edges of the signal a. When the addition of data to the file ends, the A/D converter delivers a signal indicating the end of A/D conversion. In response to this signal, the counter's value is read, and a check is performed to see whether the read value agrees with the initial value A (steps 13 and 14). If they do not agree, it follows that an error has occurred. Control then goes to step 31. If they agree, the condition is regarded as normal, and control proceeds to step 15. The MPU waits until the counter's value varies (step 16). A check is made to ascertain whether the mirror has reached the next point for measurement by checking the counter's value. If the mirror moved in the forward direction, the next point is A+1. If the mirror moved in the reverse direction, the next point is A −1(step 17). If the mirror has reached a point other than the next point for measurement, then an error has taken place. Control goes to step 31. If the mirror has reached the next point for measurement, then the count value A is replaced by A+X (step 18). Control returns to step 10, where A/D conversion is carried out.

Steps 10-18 are repeatedly performed until the count value A reaches the final value B of up/down count. At this time, all the measurement in all the points in one scan are completed. Data is collected while the movable mirror is in region e in FIG. 7. Control goes from step 12 to step 19 to accumulate data. More specifically, file of data obtained by one scan is added to the file of accumulation, for accumulating data (step 19). The number of accumulative operations F is incremented (step 20).

After a series of accumulative operations is completed, the number of errors E is reset to 0 (step 22). The direction of sliding movement of the movable mirror is reversed, and the initial value A and the final value B used for the previous scan are interchanged with each other (steps 23-26). Control goes back to step 8. The same process is repeated with the direction of sliding movement of the movable mirror reversed. This process corresponds to the process subsequent to point f in FIG. 7.

If the number of accumulative operations reaches a preset number of accumulative operations C (step 21), then Fourier transformation is made (step 27). If necessary, transmissivity and absorbance are calculated (step 28). Then, the calculated values are displayed (step 29). The sliding movement of the movable mirror is brought to a stop (step 30).

If the result of the decision made in step 14 or 17 is that an error has occurred, the number of errors E is incremented (step 31). If the number of errors does not reach the permissible value D, the mirror is slided up to the final point of sampling (steps 32-34). Control goes to step 23. The direction of movement of the movable mirror is reversed, and similar measurement are made.

If the result of decision made in step 32 is that the number of errors E has reached the permissible value D, then notation indicating an error in the sliding movement is displayed (step 35). Thus, the measurement is ended.

In the example described in connection with FIG. 2, all the operations are performed under the control of the MPU 86. Only data collection may be performed by a separate CPU that is independent of the CPU connected with the CRT 94, the external storage 92, and other components. Also, the sliding controller 20 may be controlled by executing the program introduced in the CPU. In the above example, the phase plate consists of the λ/8 plate 56. Instead, another phase plate such as a λ/4 plate or λ/2 plate may be used. The phase plate 56 may be installed between the mirror plate 6 and the beam splitter 2.

In accordance with the invention, analog data is converted into digital form when the count value of the up/down counter used for quadrature control is varied. After the A/D conversion, the counter's value is checked. If it is different from the count value obtained when analog-to-digital conversion was started, then the sliding movement of the movable mirror is determined to be abnormal. Therefore, an error in the sliding movement can be detected with sensitivities of the order of the wavelength of the light source of the control interferometer without adding further function of detecting abnormal sliding movement of the moveable mirror. Hence, data can be obtained precisely by accumulation by realizing coherent addition.

What is claimed is:

1. An interference spectrophotometer comprising:
   a beam splitter dividing an incident linearly polarized laser beam into two parts;
   a movable mirror and a fixed mirror which return the two parts of the beam to the beam splitter;
   a phase plate installed between one of the mirrors and the beam splitter;
   a polarizing beam splitter which divides the interference radiations meeting at the first-mentioned beam splitter into two;
   two detectors receiving the two polarized radiations, respectively, emerging from the polarizing beam splitter;
   an analog-to-digital converter for converting sampled signals into digital form;
   an up/down counter which receives the output signals from the two detectors and which, when the counter's value varies, produces a signal to cause the analog-to-digital converter to start analog-to-digital conversion of data associated with said counter value; and
   a decision part which checks the counter's value after the completion of the A/D conversion and which, if this value differs from the count value obtained at the beginning of the A/D conversion, determines that the movable mirror abnormally slid.

2. The interference spectrophotometer of claim 1, wherein at least one of the two detectors includes plural separate detecting elements, the spectrophotometer further including
   a means for adjusting the position of the movable mirror or the fixed mirror along a straight line normal to the movable mirror or the fixed mirror so that the phases of the interference signals detected by the detector including the plural detecting elements have a constant relation, and
   a means which superimposes plural interference signals detected by the detector including the plural detecting elements to produce an interference signal of an average phase relation.

* * * * *